(12) United States Patent
Cross, III

(10) Patent No.: US 12,029,750 B2
(45) Date of Patent: *Jul. 9, 2024

(54) FOLIC COMPOSITIONS AND METHODS FOR TREATMENT OF DIABETIC NEUROPATHIES

(71) Applicant: William H. Cross, III, Waco, GA (US)

(72) Inventor: William H. Cross, III, Waco, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/805,479

(22) Filed: Jun. 6, 2022

(65) Prior Publication Data

US 2022/0305047 A1    Sep. 29, 2022

Related U.S. Application Data

(63) Continuation of application No. 16/264,609, filed on Jan. 31, 2019, now Pat. No. 11,351,188.

(60) Provisional application No. 62/624,735, filed on Jan. 31, 2018.

(51) Int. Cl.
| | |
|---|---|
| *A61K 31/714* | (2006.01) |
| *A61K 31/14* | (2006.01) |
| *A61K 31/185* | (2006.01) |
| *A61K 31/198* | (2006.01) |
| *A61K 31/519* | (2006.01) |
| *A61P 25/02* | (2006.01) |

(52) U.S. Cl.
CPC ............ *A61K 31/714* (2013.01); *A61K 31/14* (2013.01); *A61K 31/185* (2013.01); *A61K 31/198* (2013.01); *A61K 31/519* (2013.01); *A61P 25/02* (2018.01)

(58) Field of Classification Search
CPC .... A61K 31/714; A61K 31/198; A61K 31/14; A61P 25/02
See application file for complete search history.

(56) References Cited

U.S. PATENT DOCUMENTS

| | | |
|---|---|---|
| 3,711,602 A | 1/1973 | Herschler |
| 5,719,119 A | 2/1998 | Veech |
| 7,060,295 B2 | 6/2006 | Richardson et al. |
| 7,645,742 B2 | 1/2010 | Stohs |
| 9,414,615 B2 | 8/2016 | Sridhar |
| 10,945,979 B1 | 3/2021 | Schroeder |
| 11,351,188 B2 * | 6/2022 | Cross, III ............... A61K 31/14 |
| 2001/0011083 A1 | 8/2001 | Barr et al. |
| 2001/0031744 A1 | 10/2001 | Kosbab |
| 2005/0129783 A1 | 6/2005 | McCleary et al. |
| 2011/0313043 A1 | 12/2011 | Kramer et al. |
| 2012/0232003 A1 | 9/2012 | Takahashi et al. |
| 2014/0044685 A1 | 2/2014 | Greenberg et al. |
| 2016/0228409 A1 | 8/2016 | Cross |
| 2017/0312329 A1 | 11/2017 | Cross |

FOREIGN PATENT DOCUMENTS

| | | |
|---|---|---|
| CN | 101716182 A | 6/2010 |
| CN | 101716182 | 4/2013 |
| IN | 1306CHE2007 | 1/2009 |
| WO | 2008048045 | 4/2008 |
| WO | 2013108262 | 7/2013 |
| WO | 2013108262 A1 | 7/2013 |
| WO | 2008048045 A1 | 9/2021 |

OTHER PUBLICATIONS

Bell, D.S.H., 2012, Case Report in Endocrinology, Article ID 165056, 3pp.
Curtis, L., 2013, International Journal of Diabetes Research, 2:56-60.
Hagen, M. et al., 2017, Current Medical Research and Opinion, 33(9):1623-1634.
Henriksen, E.J., 2006, Free Radical Biology Medicine, 40:3-12.
Lautt et al., 2010, Can. J. Physiol. Pharmacol., 88:313-323.
McCarty, M.F., 2017, Healthare, 5, 28pp (doi:10.3390/healthcare5010015).
Shinohara, T. et al., 2004, J. Biol. Chem., 279:23559-23564.
Vita Sciences, Nervex Neuropathy Pain Relief (Product Literature), Jan. 26, 2017.
Wagner, T., 2012, Pain Management, 2(3):239-250.
Wojtczak, A., 2002, Medical Teacher, 24:658-660.
Yonguc, et al., 2015, Gene, 555:119-126.

* cited by examiner

*Primary Examiner* — Pancham Bakshi
(74) *Attorney, Agent, or Firm* — Thomas | Horstemeyer, LLP

(57) ABSTRACT

The invention provides compositions and methods to treat diabetic neuropathies. In particular the invention has discovered that, in combination with a folic compound, particular combinations of two types of additional antioxidants have complementary effects for use against diabetic neuropathies. These include antioxidants that comprise stabilizing heteroatoms and antioxidants with an extended conjugated segment, where at least one of the antioxidants that comprises a stabilizing heteroatom also has pro-oxidant effects.

17 Claims, No Drawings

FOLIC COMPOSITIONS AND METHODS FOR TREATMENT OF DIABETIC NEUROPATHIES

CROSS-REFERENCE TO RELATED APPLICATIONS

This application is a continuation application of U.S. Nonprovisional patent Application Ser. No. 16/264,609, filed on Jan. 31, 2019, which claims the benefit of and priority to U.S. Provisional patent Application No. 62/624,735, filed on Jan. 31, 2018, the contents of which are incorporated by reference herein in their entireties.

FIELD OF THE INVENTION

The invention concerns compositions and methods for the treatment and prevention of diabetic neuropathies.

BACKGROUND

Diabetes mellitus is a carbohydrate metabolism disorder caused by insufficient insulin production and or reduced sensitivity to insulin. Consequently, the cells are inhibited from normal glucose utilization, resulting in abnormally high blood sugar levels and a variety of maladies. Chronic complications include diabetic retinopathy (retinal changes leading to blindness), kidney disease and frequent infection. Acute complications from diabetes may be fatal, such as "dead-in-bed syndrome" and such as "diabetic shock" wherein a diabetic person suddenly and without warning becomes temporarily blind, disoriented and or loses consciousness during normal activity. To date there is no cure for diabetes.

Diabetes is the leading known cause for development of neuropathy in developed countries. And in fact, diabetic neuropathy affects almost 2% of the global population and about 20% of the diabetic population and is the leading cause of morbidity and mortality in diabetes patients. It is believed to be responsible for between 50% and 75% of nontraumatic amputations. Hyperglycemia is the main risk factor, but with treatment the incidence of diabetic neuropathy is lowered almost four-fold in Type 1 diabetic patients. Other factors include the patient's age, smoking, hypertension, height and hyperlipidemia, and length of personal history with diabetes.

At an early stage, diabetic neuropathies are typically associated with microvascular injuries in which blood cells supplying nerves narrow and then capillary membranes thicken, reducing the oxygen supply to nerves and resulting in ischemia of neurons. For that reason agents that dilate blood vessels are often administered. Several other pathologies contribute. Irregularities in the polyols pathway may also contribute to microvascular damage. High glucose levels within cells also lead to non-enzymatic glycosylation of proteins, which causes inhibition of their function.

Polyneuropathies manifest in various ways. Sensorimotor polyneuropathy affects longer nerve fibers more, and reduces sensation and reflexes, appearing in the extremities first as numbness and night-time pain which may burn, ache or feel prickly.

Autonomic neuropathy affects several organ systems such as the heart, lungs, blood vessels, bones, fatty tissue, sweat glands, gastrointestinal system and genitourinary system. A common form of the disorder leads to fainting upon standing up due to orthostatic hypotension, and is also associated with respiratory sinus arrhythmia. Where the disorder affects the gastrointestinal tract it can reduce absorption of oral diabetes medications, resulting in hypoglycemia, meanwhile reduced rate of movement through the intestines can lead to bacterial overgrowth and resulting bloat, gas and diarrhea in patients with high blood sugar. Reflux nephropathy is one result for urinary symptoms, together with other outcomes when urinary retention results from urinary tract infections.

Cranial neuropathies may affect the eye's oculomotor nerve (cranial nerve #3 associated with third nerve palsy) abruptly with frontal pain, and begin with the nerve fibers furthest from the vascular supply. This affects eyelid movement and pupil constriction. Neuropathies that affect the sixth nerve, i.e., the abducens nerve, affect lateral eye movement. In some cases the fourth (trochlear) nerve is affected, associated with downward eye movement. Mononeuropathies of certain spinal nerves mimic the symptoms of myocardial infarction, cholecystitis or appendicitis. And entrapment neuropathies in diabetics commonly lead to carpal tunnel syndrome.

Generally neuropathic symptoms develop over a period of years. Symptoms vary between the disorders: they range from weakness, imbalance and muscle contraction; to sexual dysfunctions; to vision changes and impaired speech; to numbness or various types of pain or other sensations; to loss of control over the bladder or bowels.

Apart from control of blood sugar levels, treatment typically has the objective of managing pain and minimizing symptoms. The treatments employed fall into the following categories: tricyclic antidepressants (TCAs) at usually low dosages (for short-term relief of pain); serotonin-norepineprine reuptake inhibitors (SNRIs); selective serotonin reuptake inhibitor; antiepileptic drugs (AEDs, for short-term relief of pain); erythropoietin; natural remedies (e.g., supplements with vitamin B1, vitamin B12, alpha lipoic acid, and L-arginine to control pain); classic analgesics (opioids and or NSAIDs in combination with other treatments); medical devices (infrared, e.g., 890 nm to act upon cytochrome C to release nitric oxide and trigger vasodilation); and physical therapy (such as painless electric current to relieve stiffness, muscle training for gait and posture, exercise to minimize spasms and atrophy, ultrasound, etc.).

The mechanistic aspects of diabetic neuropathy are poorly understood so treatment has focused on symptom reduction though the disease is progressive. Even that is in need of improved approaches because, for instance, numbness in feet results in unwitting injuries, ulceration from small infections, and amputations. That problem's importance is evident in that sixty percent of lower extremity amputations are for diabetes patients. Moreover, the drugs used to treat diabetic neuropathy have a number of side effects users would not experience in their absence, thus: 38% of the users for diabetic neuropathic pain experience dizziness; 13% experience blurry vision and difficulty with depth perception; 9% experience increased neuropathy, i.e., a worsening of the pain at issue; and 14% become infected.

Consequently, there is an ongoing need for compositions to treat and prevent diabetic neuropathies.

SUMMARY OF THE INVENTION

The invention provides compositions and methods to treat and prevent development of diabetic neuropathies. In particular, the present invention provides compositions of folic compounds in an improved formulation comprising particular combinations of diverse types of antioxidants that have complementary effects for use against diabetic neuropathies. It has further been discovered that for purposes of the invention it is beneficial to use antioxidants that also facilitate an oxidative balance, i.e., that have pro-oxidant effects, for instance in the liver.

In a particular embodiment the invention provides an improved composition for treatment of diabetic neuropathies, wherein said composition comprises a pharmaceutically effective amount of a folic compound and a pharmaceutically effective amount of each of at least two types of additional antioxidant compounds, characterized in that
- a) a first type of additional antioxidant compound comprises a stabilizing heteroatom covalently bonded to a saturated carbon;
- b) a second type of additional antioxidant compounds comprises an extended conjugated segment having a backbone that comprises at least fourteen electrons in pi bond(s) and or heteroatom lone pair(s);

wherein:
- i) at least one of the first type of additional antioxidant compounds also has a pro-oxidant effect; and
- ii) as measured by a scale known as the Neuropathic Pain Scale, a pharmaceutically effective amount of the composition is effective to decrease a user's diabetic neuropathic pain by at least 50 percent within 3 to 5 days after the onset of administration.

In a further embodiment the invention provides a method for treatment of diabetic neuropathy, said method comprising administering to a patient who has a diabetic neuropathy a composition that comprises a pharmaceutically effective amount of a folic compound and a pharmaceutically effective amount of each of at least two types of additional antioxidant compounds, characterized in that:
- a) a first type of antioxidant compound comprises a stabilizing heteroatom covalently bonded to a saturated carbon; and
- b) a second type of antioxidant compound comprises an extended conjugated segment having a backbone that comprises at least fourteen electrons in pi bond(s) and or heteroatom lone pair(s);

wherein:
- i) at least one of the first type of additional antioxidant compounds also has a pro-oxidative effect; and
- ii) as measured by a scale known as the Neuropathic Pain Scale, a pharmaceutically effective amount of the composition is effective to decrease a user's diabetic neuropathic pain by at least 50 percent within 3 to 5 days after the onset of administration.

DETAILED DESCRIPTION OF THE INVENTION

The invention may be further understood by consideration of the following definitions for the terms as used herein.

The term "diabetic" refers to the metabolic disorder diabetes mellitus and or its symptoms, and has its usual and ordinary meaning in the medicinal arts. The term includes each of the known types of diabetes including the classically defined categories of gestational diabetes, type 1 diabetes (from birth), and type 2 diabetes (later onset). The term "diabetic" further includes the five more recently classified genetically distinct groupings of patients, as follows. Cluster 1, currently known as type 1, pertains to severe autoimmune diabetes; it is characterized by insulin deficiency and the presence of autoantibodies; it has been identified in 6-15 percent of subjects. Cluster 2 pertains to severe insulin-deficient diabetes; it is characterized by younger age, insulin deficiency, and poor metabolic control, but no autoantibodies; it has been identified in 9-20 percent of subjects. Cluster 3 pertains to severe insulin-resistant diabetes; it is associated with a significantly higher risk of kidney disease and was identified in 11-17 percent of subjects. Cluster 4 pertains to mild obesity-related diabetes, most common in obese individuals, and has been identified in 18-23 percent of subjects. Cluster 5 pertains to mild age-related diabetes, especially in elderly individuals, and has been identified in 39-47 percent of subjects.

The term "diabetic neuropathy" as used herein has its usual and ordinary meaning in the medicinal arts means peripheral neuropathy due to diabetes mellitus.

The term "symptom" as used with respect to diabetic neuropathy means a symptom thereof. Numerous such symptoms are well known in the medical arts and include but are not limited to those that arise from: microvascular injuries; irregularities in the polyols pathway; and non-enzymatic glycosylation of proteins. Non-limiting examples of symptoms of neuropathies in diabetic patients include: numbness; night-time pain which may burn, ache, or feel prickly;

fainting upon standing up due to orthostatic hypotension; respiratory sinus arrhythmia; hypoglycemia; bacterial overgrowth due to reduced rate of movement through the intestines and resulting in bloat, gas and diarrhea; reflux nephropathy and other outcomes when urinary tract infections cause urinary retention; frontal pain from the eye's oculomotor nerve (e.g., third nerve palsy); effects on eyelid movement and pupil constriction; sixth-nerve effects on lateral eye movement; fourth-nerve effects on downward eye movement; spinal nerve effects that mimic the symptoms of myocardial infarction, cholecystitis, and or appendicitis; and carpal tunnel syndrome due to an entrapment neuropathy; weakness; imbalance; muscle contraction; sexual dysfunction; vision changes; impaired speech; pain and other sensations; loss of control over the bladder; and loss of control over the bowels. The term "symptom" as used with respect to diabetic neuropathy is not limited by the time over which the symptom develops, regardless of whether its appearance is sudden or over a period of years.

The term "effective to reduce" as used with respect to medicinal treatment of a symptom of a diabetic neuropathy means that the compound is effective to decrease the duration or magnitude of the symptom. The term "effective to mitigate" as used with respect to medicinal treatment of a symptom of a diabetic neuropathy means that the compound is effective to decrease the discomfort or appearance that results from the symptom. The term "effective to reduce or mitigate" as used with respect to medicinal treatment of a symptom of a diabetic neuropathy does not exclude the use of any compound that both reduces and mitigates such a symptom.

The term "Neuropathic Pain Scale" or "NPS" refers to a well-validated survey-like tool in the medical arts as used to measure neuropathic pain and a drug's effectiveness in reducing and or mitigating it. For the NPS the patient scores each of ten dimensions of pain on a scale of 1 to 10, those dimensions being: intensity; sharpness; hotness; dullness; coldness; skin sensitivity; itchiness; unpleasantness; intensity of the deep and surface pains; and duration (sporadic/intermittent, constant, or constant in the background but with flare-ups). Summing up these items gives a 100-point scale for pain. A useful benchmark of effectiveness for the present invention is that the composition lowers the perceived diabetic neuropathic pain by 50% within 3 to 5 days after the onset of administration, and virtually eliminates the pain when used daily over a period of several weeks. In certain embodiments the pain being measured is a particular pain in a particular bodily location, for instance one of: pain, burning or tingling in the feet; aching hands; painful fingers; pain in legs; back pain; retinopathy; or sciatic nerve pain.

The term "composition" as used with respect to a composition for treatment of a diabetic neuropathy means a formulation comprising one or more medicinal substances that are individually or alternatively collectively effective to minimize symptoms of a diabetic neuropathy.

The term "folic compound" as used herein refers to a substance from the following group: folic acid ((2S)-2-[[4-[(2-Amino-4-oxo-1H-pteridin-6-yl)methylamino]benzoyl]amino]pentanedioic acid), dihydrofolic acid (N-(4-{[(2-amino-4-oxo-1,4,7,8-tetrahydropteridin-6-yl)methyl]amino}benzoyl)-L-glutamic acid), tetrahydrofolic acid ((2S)-2-{[4-({[(6R)-2-amino-4-oxo-1,4,5,6,7,8-hexahydropteridin-6-yl]methyl}amino)phenyl]formamido}pentanedioic acid), and L-5-methyltetrahydrofolate ((2S)-2-[[4-[(2-amino-5-methyl-4-oxo-1,6,7,8-tetrahydropteridin-6-yl)methylamino]benzoyl]amino]pentanedioic acid), and pharmaceutically acceptable salts and esters and mixtures of any of the above folic compounds. Folic acid is also known as Vitamin $B_9$, Vitamin $B_C$, vitamin M, folacin, and pteroyl-L-glutamate. L-5-methyltetrahydrofolate is also known as levomefolic acid, L-5-MTHF, (6S)-5-MTHF, L-methylfolate, and L-5-methyltetrahydrofolate. A particularly useful folic compound for the present invention is calcium levomefolate, for which a proprietary name is Metafolin® from Merck KGaA, however the invention is not so limited.

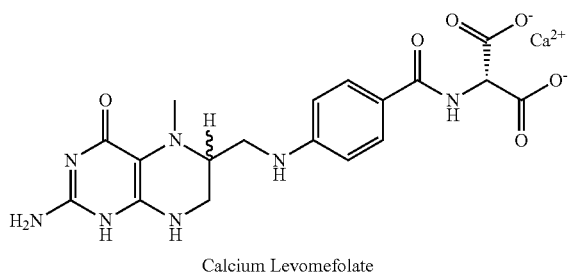

Calcium Levomefolate

The term "pharmaceutically effective amount" as used with respect to antioxidants, medicinal compounds or their salts or esters means that the respective compound(s), salt(s) or ester(s) are pharmaceutically safe and effective at the dose given. Examples of counterions and ester groups that are acceptable for pharmaceutical use are found, for instance, in editions of Remington's Pharmaceutical Sciences. Medicinal compounds for which such pharmaceutically effective amounts are particularly applicable in the present invention are folic compounds.

The terms "salts" and "esters" have their usual and ordinary meaning in organic chemistry. The term "mixtures" as used with respect to folic compounds and their salts and esters means that more than one such compound is present and that the multiple such compounds are mixed, whether they are folic compounds and or their salts and or esters.

The terms "antioxidant" and "antioxidant compound" are used interchangeably and refer to compounds that inhibit formation of free radicals by biochemical or other chemical oxidation. The term antioxidant has its usual and ordinary meaning in the chemical and medical arts.

The term "saturated carbon" as used herein refers to a carbon atom that has no multiple bonds.

The term "covalently bonded" has its usual and ordinary meaning in organic chemistry.

The term "stabilizing heteroatom" as used with respect to an atom in an antioxidant molecule means that the atom in view is an atom other than carbon, hydrogen or a metal in an organic molecule, and that the heteroatom is able to stabilize a radical formed on a neighboring saturated carbon such as by donation of electron density into it, or by rearrangement of the unpaired electron within the molecule. In particular embodiments heteroatoms N (nitrogen), S (sulfur), and or O (oxygen) are preferred in the stabilizing moiety—or moieties—in an antioxidant compound. Examples of a neighboring, i.e., adjacent, saturated hydrocarbon include —$CH_2R$, —$CHR^1R^2$, and —$CH_3$, where the R species are atoms or functional groups known in organic chemistry. Preferred examples of antioxidant compounds comprising a stabilizing heteroatom adjacent to a saturated hydrocarbon include taurine, beta-alanine, citrulline, and acetyl-L-carnitine, and in certain particularly preferred embodiments include the use of a mixture of all four.

The term "extended conjugated segment" as used with respect to an antioxidant molecule means that at least a portion of the molecule has an alternating arrangement of single and double bonds, and that the arrangement comprises at least 14 (fourteen) pi electrons in pi bonds and or heteroatom lone pairs in series on a molecule. As used herein the term contemplates that the backbone of the extended conjugated segment is composed of carbon atoms, except however the backbone may include one or more heteroatoms, each being singly covalently bonded to neighboring carbon atoms or at the end of a chain of carbon atoms. The term "participating in a ring system" as used with respect to pi electrons means that there bonds are part of or define an aromatic or heteroaromatic ring. Examples of such systems with all-carbon backbones include carotenoids and aromatic and anti-aromatic rings. In a certain embodiment a heteroatom may be covalently double-bonded to a neighboring carbon atom and covalently single-bonded to another neighboring carbon atom, all in the extended conjugated segment. In another embodiment a heteroatom may be covalently single-bonded to each of two or three neighboring carbon atoms, but there the heteroatom has a lone pair of electrons that may participate in pi-bond delocalization as those terms are understood in organic chemistry. Examples of systems with carbon double bonds to heteroatoms in a backbone, and or with heteroatom lone pair participation in pi-bond delocalization, include pyrrole rings such as are found in hemoglobin and chlorophylls, and corrin rings such as are found in cobalamin compounds. In another embodiment a keto or enol moiety may be present in the extended conjugated segment, effectively interrupting the alternating series of single and double bonds except that keto-to-enol and enol-to-keto transitions allow for participation of the moiety in delocalization to either side of the moiety. Examples of systems with keto-enol tautomers include the curcuminoids.

The term "pro-oxidant" as used herein refers to a compound that has the ability to promote an oxidation reaction. Some antioxidant compounds act as pro-oxidants under some conditions. In a preferred embodiment the pro-oxidant activity takes place in liver tissue however the invention is not so limited. A preferred embodiment of an antioxidant compound that has a pro-oxidant effect is taurine. In certain embodiments of the invention taurine is in a mixture with at least one additional antioxidant that has a pro-oxidant effect. The term pro-oxidant as used herein includes but is not limited to compounds for which the ability to be a pro-oxidant is contingent upon conditions, such as whether dioxygen or transition metals are present. Such conditional behavior typically arises where reduction of dioxygen or peroxides is spin-forbidden and thus requires the presence of an intermediate such as a reduced transition metal—which is generated from a higher oxidation state of the metal by the action of the conditional pro-oxidant—in order to reduce the dioxygen or peroxide and have the pro-oxidant effect. The term "conditional pro-oxidant" as used herein refers to such condition-dependent pro-oxidant properties.

The term "cobalamin compound" means cobalamin—also known as Vitamin $B_{12}$—and its derivatives and variants such as salts, esters, and those defined by the bonding arrangement of functional groups at the compound's cobalt atom. Preferred cobalamin compounds have the compound's cobalt atom covalently bonded to -5'-deoxyadenosyl, —$CH_3$, —OH, or —CN; these are respectively adenosyl-cobalamin, methylcobalamin, hydroxocobalamin, and cyanocobalamin. Methylcobalamin is particularly preferred but the invention is not so limited.

The term "method of treatment" as used with respect to diabetic neuropathies contemplates therapeutic treatments as well as preventative treatments.

The terms "administering" and "administration" as used with respect to compounds to treat diabetic neuropathy is not limited by the type of their physical dosing, whether it is oral, buccal, parenteral, transdermal, or some other method of administering a dose.

The invention has found that folic compounds have complementary effects with diverse types of additional antioxidants to reduce or mitigate the symptoms of diabetic neuropathies. In particular it is beneficial to use a folic compound in combination with an antioxidant that comprises a stabilizing heteroatom and an antioxidant that has an extended conjugated segment. It has further been discovered that for purposes of the invention it is beneficial if one of the additional antioxidant facilitates an oxidative balance, i.e., has a pro-oxidant effect. A non-limiting example of sites for the pro-oxidant effect is the liver. And in fact folic compounds also have a pro-oxidant effect.

Particularly suitable compositions for the invention include a combination of each of the ingredients indicated in Table I in the amounts shown. But note that though the structure and properties of folic acid are shown in Table I that molecule is simply representative of folic compounds as a class, and that for instance the folic compound can be calcium levomefolate or another folic compound.

TABLE I

| Compound Description and Use | Structure |
|---|---|
| A folic compound in a range of ≥100 μg; non-limiting illustrative ranges are 100 to 5,000 μg; a non-limiting illustrative quantity is 500 μg. By way of illustrating the properties of folic compounds, folic acid is an antioxidant that comprises stabilizing heteroatoms, conjugated segments and phenolic-like groups. Likewise by way of comparison folic acid acts as an antioxidant in early-stage peroxidation, e.g., of linoleic acid but as a pro-oxidant in late stage peroxidation of the same. | 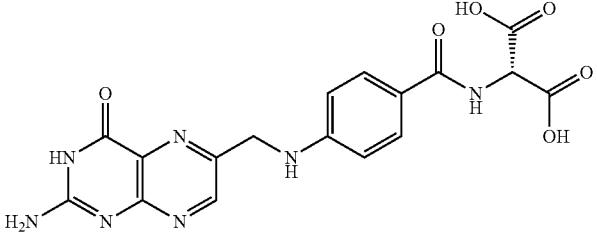<br>Folic Acid |
| Taurine in a range of 40 to 360 mg; a non-limiting illustrative quantity is 200 mg. Taurine is an antioxidant that comprises a stabilizing heteroatom, relieves oxidative stress, and has a pro-oxidative effect in the liver. | 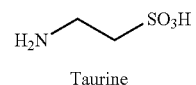<br>Taurine |
| Beta-alanine in a range of 10-90 mg; a non-limiting illustrative quantity is 50 mg. Beta-alanine is an antioxidant that comprises a stabilizing heteroatom. However beta-alanine does not interfere with the balance between antioxidants and pro-oxidants in the tissues where is administered. | 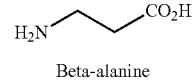<br>Beta-alanine |
| L-Citrulline in a range of 20 to 180 mg; a non-limiting illustrative quantity is 100 mg. Citrulline, an alpha-amino acid, is an antioxidant that comprises a stabilizing heteroatom, relieves oxidative stress in endothelial tissue, and is an essential substrate in enhancing NO-depending signaling. | 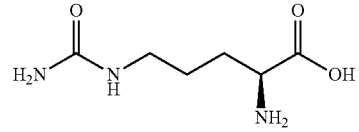<br>Citrulline |
| Acetyl-L-carnitine in a range of 40 to 360 mg; a non-limiting illustrative quantity is 200 mg. Acetyl-L-carnitine is an antioxidant that comprises a stabilizing heteroatom, relieves oxidative stress, and has a pro-oxidative effect in the liver. | 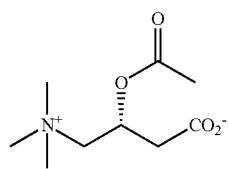<br>Acetyl-L-carnitine |

TABLE I-continued

| Compound Description and Use | Structure |
|---|---|
| Methylcobalamin (a form of Vitamin $B_{12}$) in a range of 40 to 440 μg; a non-limiting illustrative quantity is 240 μg. Methylcobalamin is an antioxidant that comprises a conjugated segment; the segment contains nitrogen atoms and among other properties can bind the oxidant nitric oxide (NO). | Methylcobalamin |

As to folic compounds, by way of comparison, conventional use for nutrition adequate intakes (AI) of folic acid have conventionally been regarded as follows: 65 mcg (micrograms, also designated herein as μg) for infants 0-6 months and 80 mcg for infants 7-12 months of age. The recommended dietary allowances (RDAs) for folate in dietary folate equivalents, including both food folate and folic acid from fortified foods and supplements are: children 1-3 years, 150 mcg; children 4-8 years, 200 mcg; children 9-13 years, 300 mcg; adults over 13 years, 400 mcg; pregnant women, 600 mcg; and breast-feeding women, 500 mcg. The tolerable upper intake levels (UL) of folate are 300 mcg for children 1-3 years of age, 400 mcg for children 4-8 years, 600 mcg for children 9-13 years, 800 mcg for adolescents 14-18 years, and 1,000 mcg for anyone over 18 years of age.

By way of comparison, commonly used daily doses of folic acid for other indications have typically been as follows: 250-1,000 mcg (to remedy folic acid deficiency); 200-500 mcg (to improve responses to medications for depression); 400 mcg to 4 mg (to prevent neural tube defects; and to reduce the risk of colon cancer); 500 mcg to 15 mg (to treat high blood levels of homocysteine); 1-5 mg (to reduce the toxicity of methotrexate therapy); 2.5 mg (to prevent macular degeneration); and 5 mg (twice daily for vertigo).

Suitable doses for folic compounds other than folic acid can be determined by applying the compound's respective ratio of molecular weight relative to that of folic acid.

For the present invention it has been found useful to administer a dose of at least 100 μg of a folic compound to an adult patient. Other embodiments include a dose in a range of: 100 to 1,000 μg; 200 to 800 μg; 300 to 700 μg; 400 to 600 μg; or about 500 μg.

The use of one or more additional antioxidants that comprise a stabilizing heteroatom adjacent to a saturated carbon atom may include taurine, beta-alanine, citrulline and acetyl-L-carnitine, and is particularly preferred in combination but the invention is not so limited. In certain preferred embodiments the composition provides an amount of taurine in the ranges of: 40 to 360 mg; 80 to 320 mg; 120 to 280 mg; 160 to 240 mg; or about 200 mg. In various preferred embodiments the composition provides an amount of beta-alanine in the ranges of: 10 to 90 mg; 20 to 80 mg; 30 to 70 mg; 40 to 60 mg; or about 50 mg. In some preferred embodiments the composition provides an amount of citrulline in the ranges of: 20 to 180 mg; 40 to 160 mg; 60 to 140 mg; 80 to 120 mg; or about 100 mg. In particular preferred embodiments the composition provides an amount of acetyl-L-carnitine in the ranges of 40 to 360 mg; 80 to 320 mg; 120 to 280 mg; 160 to 240 mg; or about 200 mg.

Other examples of such additional antioxidants that comprise a stabilizing heteroatom adjacent to a saturated carbon atom include theanine and melatonin. In certain preferred embodiments the composition provides an amount of theanine in the ranges of: 15 to 155 mg; 35 to 135 mg; 55 to 115 mg; 75 to 95 mg; or about 85 mg. In some preferred embodiments the composition provides an amount of melatonin in the ranges of: 1 to 50 mg; 5 to 40 mg; 9 to 30 mg; 13 to 20 mg; or about 15 mg. Table II below describes their properties, non-limiting illustrative dose ranges for purposes of the invention, and structures.

TABLE II

| Compound Description and Use | Structure |
| --- | --- |
| Theanine in a range of 15-155 mg; a non-limiting illustrative quantity is 85 mg. Theanine is an antioxidant that comprises a stabilizing heteroatom and relieves oxidative stress. | 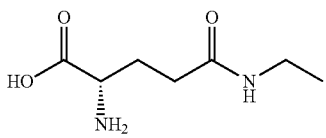<br>Theanine |
| Melatonin in a range of 1-50 mg; a non-limiting illustrative quantity is 15 mg. Melatonin is a weak antioxidant containing a stabilizing heteroatom and conjugated segment. It is a highly efficient direct free-radical scavenger; also stimulates antioxidant enzymes; reduces the activation of pro-oxidant enzymes; yet maintains homeostasis in the mitochondria, where 90% of the body's oxidation activity occurs. Melatonin is a conditional pro-oxidant. | 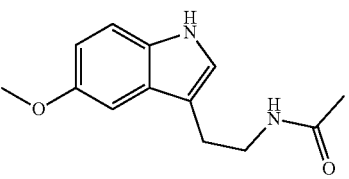<br>Melatonin |

The use of one or more additional antioxidants that comprise a conjugated segment includes cobalamin compounds, carotenoids, curcuminoids, porphyrin ring compounds, corrin ring compounds and the like. In particular it has been useful to include cobalamin compounds in compositions of the invention. In certain preferred embodiments the composition provides a cobalamin compound in the ranges of: 40 to 440 µg; 80 to 400 µg; 120 to 360 µg; 160 to 320 µg; 200 to 280 µg; or about 240 µg. In some preferred embodiments the cobalamin compound is methylcobalamin. For context, for an illustrative carotenoid such as beta-carotene, typical daily consumption is often: 6 to 15 mg per day for adults, and 3 to 6 mg per day for children. Also for context, for an illustrative curcuminoid such as curcumin, typical daily consumption is often 40 to 100 mg per day for adults, and 20 to 40 mg per day for children. However, for purposes of the present invention it is useful to provide the carotenoid, curcuminoid, porphyrin or corrin ring compound in the same ranges that would be provided for the cobalamin compound, e.g., 20 to 220 µg.

In certain embodiments the composition comprises an antioxidant bearing a phenolic or phenolic-like group. Non-limiting illustrative embodiments include at least one phenolic compound such as gallic acid, gallocatechin, catechingallate, epigallocatechin, epicatechingallate, and or epigallocatechingallate. In certain non-limiting illustrative embodiments the composition provides one or more of these compounds in a range: 5 to 500 mg; 50 to 400 mg; 100 to 300 mg; 150 to 250 mg; or about 200 mg.

By way of example a phenolic-like group is an aromatic or heteroaromatic ring that has a pendant group containing a heteroatom; examples of such pendant groups include —$ZH_{a\geq1}$ and —$ZHR_{a\geq1}$, where Z is a heteroatom such as N, S, or where the ring is heteroaromatic, O.

In certain embodiments the composition comprises an antioxidant that bears a disulfide bond. A non-limiting illustrative embodiment of such a compound is alpha-lipoic acid.

In some embodiments the composition comprises an antioxidant in which a hydrogen atom may be readily abstracted from a heteroatom that is not pendant upon an aromatic or heteroaromatic ring. Nonlimiting illustrative embodiments of such antioxidants include those with sulfhydryl (—SH) groups, such as cysteine and glutathione.

In certain embodiments compositions of the invention comprise one or more adjuvants. Non-limiting illustrative examples of such adjuvants include: analgesic adjuvants; inorganic compounds such as aluminum and or phosphate compounds; a mineral oil such as paraffin oil; dead bacteria such as *Bordetella pertussis, Mycobacterium bovis*, and toxoids; organic compounds such as squalene; delivery systems such as detergents; plant saponins; cytokines; combinations such as Freund's complete or Freund's incomplete adjuvant; and food-based oils such as Adjuvant 65, which is based on peanut oil. The terms in this paragraph are used with their usual and ordinary meaning in the art of formulation for drugs and dietary supplements.

In various embodiments compositions of the invention comprise one or more excipients. Non-limiting illustrative examples of such excipients include: antiadherents, binders, coatings, colors; disintegrants; flavors; glidants; lubricants; preservatives; sorbents; sweeteners; and vehicles. The terms in this paragraph are used with their usual and ordinary meaning in the art of drug formulation.

There are several survey-like tools to measure neuropathic pain and a drug's effectiveness in reducing and or mitigating it. The Neuropathic Pain Scale is particularly well-validated. For the NPS the patient scores each of ten dimensions of pain on a scale of 1 to 10, those dimensions being: intensity; sharpness; hotness; dullness; coldness; skin sensitivity; itchiness; unpleasantness; intensity of the deep and surface pains; and duration (sporadic/intermittent, constant, or constant in the background but with flare-ups). Summing up these items gives a 100-point scale for pain. A useful benchmark of effectiveness for the present invention is that the composition lowers the perceived diabetic neuropathic pain by 50% within 3 to 5 days after the onset of administration, and virtually eliminates the pain when used daily over a period of several weeks. In certain embodiments the pain being measured is a particular pain in a particular bodily location, for instance one of: pain, burning or tingling in the feet; aching hands; painful fingers; pain in legs; back pain; retinopathy; or sciatic nerve pain.

Consideration of Table III and the Examples may further clarify the scope of the invention.

TABLE III

| EXAMPLE | FOLIC COMPOUND | HETEROATOM-STABILIZED ANTIOX. | EXTENDED-CONJUGATION ANTIOX. | ANTIOXIDANTS FROM OTHER CATEGORIES |
|---|---|---|---|---|
| 1 | 500 µg calcium levomefolate | 200 mg taurine<br>50 µg beta-alanine<br>100 mg citrulline<br>200 mg acetyl-L-carnitine | 240 µg methylcobalamin | |
| 2 | 100 µg folic acid | 40 mg taurine<br>10 mg beta-alanine<br>20 mg citrulline<br>40 mg acetyl-L-carnitine | 40 µg 5-adenosyl-cobalamin | |
| 3 | 1,000 µg folic acid | 360 mg taurine<br>90 mg beta-alanine<br>360 mg acetyl-L-carnitine | 440 µg cyanocobalamin | |
| 4 | 200 µg Dihydrofolic acid | 60 mg taurine<br>70 mg beta-alanine<br>30 mg citrulline<br>300 mg acetyl-L-carnitine | 340 µg hydroxo-cobalamin | |
| 5 | 300 µg Tetrahydrofolic acid | 240 mg taurine<br>75 mg beta-alanine<br>45 mg citrulline<br>50 mg acetyl-L-carnitine | 300 µg beta-carotene | |
| 6 | 400 µg Levomefolic acid | 200 mg Acetyl-L-carnitine | 140 µg curcumin | |
| 7 | 100 mg diethyl carboxylic ester of levomefolic acid | 220 mg taurine<br>85 mg theanine | 130 µg xanthophyll and 280 µg corrole | 200 mg epigallocatechin-gallate |
| 8 | 900 mg 100 mg sodium levomefolate | 15 mg melatonin | 200 µg porphin and 40 µg chlorophyll A | |
| 9 | 100 mg potassium levomefolate | 400 mg taurine<br>150 mg beta-alanine<br>50 mg citrulline<br>100 mg acetyl-L-carnitine | 90 µg corrin and 160 µg heme | 120 µg Alpha-lipoic acid |
| 10 | 700 µg Tetrahydrofolic acid | 150 mg taurine<br>75 mg acetyl-L-carnitine<br>15 mg melatonin | 380 µg protoporphyrin IX | |

EXAMPLE 11

A solid dose in the form of a gel capsule was prepared containing 500 µg calcium levomefolate, 200 mg taurine, 50 mg beta-alanine, 100 mg citrulline, 200 mg acetyl-L-carnitine, and 240 µg methylcobalamin, together with silica and magnesium stearate. The patient was a college-age type 1 diabetic male with a persistent history of diabetic neuropathic pain. For the first five days the patient took a capsule every 2 to 4 hours as needed, for a total of 4 to 6 capsules per day, and thereafter took a capsule every 2 to 6 hours as needed, for a total of 2 to 6 capsules per day. Pain was noted to decrease by at least 50% within the first 36 hours, and to be virtually eliminated over a period of about one week of taking 2 to 6 capsules per day as needed. Ceasing to use the formula resulted in the return of symptoms over the course of 72 hours, and these were noticeable even by the end of the first day of non-use.

EXAMPLE 12

The same composition as in Example 11 was administered to a type 1 diabetic male patient in his mid-30s. He had a history of taking metformin hydrochloride alone, yet substantial neuropathic pain persisted. The patient experienced drastic pain relief after four days, i.e., the pain decreased by more than 50%, and his relief continued to improve over a two-week period until the pain was virtually eliminated. After a month of use the patient ceased taking the invention composition; as a result the neuropathic pain returned over the course of a week.

In general, virtual elimination of the pain symptoms is to be expected over a break-in period of one week to one month, with little or no pain thereafter as long as the daily dosing with the composition continues to be maintained.

The embodiments of the invention as described herein are merely illustrative and are not exclusive. Numerous additions, variations, derivations, permutations, equivalents, combinations and modifications of the above-described invention will be apparent to persons of ordinary skill in the relevant arts and are within the scope and spirit of the invention. The invention as described herein contemplates the use of those alternative embodiments without limitation.

The invention claimed is:

1. A composition comprising a folic acid compound and:
   a) a first antioxidant component comprising (i) taurine, (ii) acetyl-L-carnitine, and (iii) at least one of citrulline, theanine, and melatonin;
   b) a second antioxidant component comprising a cobalamin compound.

2. The composition of claim 1, wherein the folic compound is selected from the group consisting of folic acid, dihydrofolic acid, tetrahydrolic acid, levomefolic acid, and their pharmaceutically acceptable salts and esters and mixtures thereof.

3. The composition of claim 1, wherein the folic compound is calcium levomefolate.

4. The composition of claim 1, wherein the first antioxidant component comprises taurine, beta-alanine, citrulline, and acetyl-L-carnitine.

5. The composition of claim 1, wherein the second antioxidant component is selected from the group consisting of 5-adenosylcobalamin, methylcobalam in, hydroxocobalam in, and cyanocobalamin.

6. The composition of claim 1, wherein the second antioxidant component is methylcobalamin.

7. The composition of claim 1, wherein the first antioxidant component comprises taurine, beta-alanine, citrulline, and acetyl-L-carnitine, and the second antioxidant component is methylcobalamin.

8. The composition of claim 1, wherein the first antioxidant component comprises taurine, beta-alanine, citrulline, and acetyl-L-carnitine, the second antioxidant component is methylcobalamin, and the folic compound is calcium levomefolate.

9. The composition of claim 1 wherein the composition comprises:
   a) a folic compound in an amount of 100 μg to 5,000 μg;
   b) taurine in an amount selected from the range of 40 to 360 mg;
   c) beta-alanine in an amount selected from the range of 10 to 90 mg;
   d) citrulline in an amount selected from the range of 20 to 180 mg;
   e) acetyl-L-carnitine in an amount selected from the range of 40 to 360 mg;
   f) methylcobalamin in an amount selected from the range of 40 to 440 μg.

10. The composition of claim 1 wherein the composition comprises:
    a) calcium levomefolate in an amount of 500 μg;
    b) taurine in an amount of 200 mg;
    c) beta-alanine in an amount of 50 mg;
    d) citrulline in an amount of 100 mg;
    e) acetyl-L-carnitine in an amount of 200 mg;
    f) methylcobalamin in an amount of 240 μg.

11. The composition of claim 1, wherein the composition further comprises a phenolic compound selected from the group consisting of gallic acid, gallocatechin, catechingallate, epigallocatechin, epicatechingallate, and epigallocatechingallate.

12. The composition of claim 11, wherein the phenolic compound is in an amount from 5 mg to 400 mg.

13. A method for treatment of diabetic neuropathy, said method comprising administering to a patient who has a diabetic neuropathy the composition of claim 1.

14. The method of claim 13, wherein the composition treats one or more symptoms of diabetic neuropathy, wherein the symptom comprises numbness; night-time pain; fainting upon standing up due to orthostatic hypotension; respiratory sinus arrhythmia; hypoglycemia; bacterial overgrowth due to reduced rate of movement through the intestines; intestinal bloat, intestinal gas; diarrhea; reflux nephropathy; frontal pain from the eye's oculomotor nerve; effects on eyelid movement and pupil constriction; sixth-nerve effects on lateral eye movement; fourth-nerve effects on downward eye movement; spinal nerve effects that mimic the symptoms of myocardial infarction, cholecystitis, and or appendicitis; carpal tunnel syndrome due to an entrapment neuropathy; weakness; imbalance; muscle contraction; sexual dysfunction; vision changes; impaired speech; pain and other sensations; loss of control over the bladder; and loss of control over the bowels.

15. The method of claim 13, wherein the composition decreases the patient's diabetic neuropathic pain by at least 50 percent within 3 to 5 days after the administration of the composition.

16. The method of claim 13, wherein the composition is in a capsule, wherein the capsule is administered to the subject every 2 to 6 hours.

17. The method of claim 13, wherein the composition is in a capsule, wherein the patient is administered 4 to 6 capsules per day.

* * * * *